(12) United States Patent
Sunako

(10) Patent No.: US 6,551,257 B1
(45) Date of Patent: Apr. 22, 2003

(54) BIOELECTRICAL IMPEDANCE MEASURING APPARATUS WITH HANDGRIP

(75) Inventor: Kiharu Sunako, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/684,619

(22) Filed: Oct. 10, 2000

(30) Foreign Application Priority Data

Oct. 12, 1999 (JP) ............................................. 11-290033

(51) Int. Cl.[7] ........................... A61B 5/103; A61B 5/117
(52) U.S. Cl. ................................................... 600/587
(58) Field of Search ................................ 600/587, 547, 600/372, 548; 128/639, 734, 696

(56) References Cited

U.S. PATENT DOCUMENTS 5,720,296 A 2/1998 Cha
5,817,031 A * 10/1998 Masuo et al. ............... 600/547

FOREIGN PATENT DOCUMENTS

| EP | 0 715 829 | 6/1996 |
|---|---|---|
| JP | 5-49050 | 7/1993 |
| JP | 5-337096 | 12/1993 |
| JP | 10-258041 | 9/1998 |
| JP | 11-178806 | 7/1999 |
| JP | 11-178807 | 7/1999 |

OTHER PUBLICATIONS

"Assessment of fat–free mass using bioelectrical impedance measurements of the human body [1,2]", Henry C. Lukaski, PhD, et al., The American Journal of Clinical Nutrition 41, Apr. 1985, pp. 810–817.

* cited by examiner

*Primary Examiner*—Max F. Hindenburg
*Assistant Examiner*—Brian Szmal

(57) ABSTRACT

Disclosed is a handgrip for use in bioelectrical impedance measurement that allows the measurement always in stable contact condition, irrespective of the size of a hand of a person under test. Also disclosed is a body fat measuring apparatus operated based upon the bioelectrical impedance measurement using such handgrip. The handgrip is constructed such that a grip section of the handgrip that the person grasps with his hand is gradually increased in diameter from one end to another end. The grip section is provided with a current supplying electrode and a voltage measurement electrode both disposed in the axial direction. The electrodes are spaced apart to each other by the predetermined distance. The handgrip further includes an auxiliary member coupled with the grip section.

4 Claims, 5 Drawing Sheets

BIOELECTRICAL IMPEDANCE MEASURING APPARATUS WITH HANDGRIP

BACKGROUND OF THE INVENTION

1. Field of the Invention

The present invention relates to an apparatus for measuring body composition of a human body, based on bioelectrical impedance measurement, and more particularly, to construction of a handgrip for such apparatus adapted for making contact with a body of a person under test for collecting the living body information. The handgrip is generally incorporated into any measuring apparatus based on the bioelectrical impedance measurement. Such measuring apparatus then derives the body information of the person, such as those including a body fat percentage representing a rate of fat relative to the total weight of the person and an amount of body fat representing the weight of the fat.

2. Description of the Prior Art

It is already known to estimate body composition of a human body from the measurement of living body impedance. For instance, it has been found in an article "Assessment of fat-free mass using bioelectrical impedance measurement of the human body", *The American Journal of Clinical Nutrition*, 41 (4) 810–817, 1985. This principle of operation may be applied to measure the amount of body fat for a person under test. For instance, any impedance between extreme parts of the person such as hands and feet may be measured according to four-terminal electrode measurement theory. The impedance thus measured, together with the personal body information such as the weight, height, sex and age of the person under test, can be used to estimate the amount of body fat for the person. TOKUKOUHEI No. 5-49050 discloses an apparatus for measuring the weight of a person under test concurrent with the amount of body fat. A various types of apparatus utilizing such principle have already been put into the market.

A body fat measuring apparatus based on such bioelectrical impedance measurement is constructed in such manner that electrodes are directly made contact with a skin of a person. Then very small AC current is actually passed through the body of the person for measuring the body fat percentage and the amount of body fat for the person. Therefore, the measuring apparatus includes the electrodes adapted for contact with the specified parts of the person under test to get the living body information.

Such electrodes are generally designed to contact with a sole or a palm of the person. In case of the electrode to contact with the sole, it is mounted on the measuring apparatus and the person under test can make contact with the electrode at substantially constant pressure under the weight of the person. On the other hand, for the electrode to contact with the palm, it is constructed for the person to grasp a handgrip on which the electrode is mounted. Therefore, depending on how to grasp the handgrip or how to apply the force thereto by the person under test, the measuring conditions would be greatly changed.

For instance, TOKUKAIHEI No. 11-178806 discloses a grip, as shown in FIG. 6 of the accompanying drawings. Referring to FIG. 6, this grip is substantially in the form of a cylinder in which an applying electrode 73 and a measuring electrode 74 are disposed spaced apart to each other along the longitudinal axis of the cylinder. The applying electrode 73 applies a high frequency signal through a palm of a person under test who grasps the grip 72.

The measuring electrode 74 is mounted for measuring a potential across the body resistance also through the palm of the person who grasps the grip 72. The grip 72 is detachably connected to the main measuring apparatus via an electric wire 75.

A recess 72A is formed between the applying electrode 73 and the measuring electrode 74 for placing the middle finger of the person.

More specifically, when the person under test grasps the grip 72, he grasps an upper grip section 72B on which the applying electrode 73 is mounted with his index and thumb fingers. At the same time, he grasps a lower grip section 72C on which the measuring electrode 74 is mounted with his medical and little fingers.

Furthermore, in order not to wrongly grasp the upper and lower grip sections by the person, the lower grip section 72C is formed longer than: the upper grip section 72B in the axial direction.

For instance, the upper grip section 72B has the length equal to the width of one finger plus some margin, but the lower grip section 72C has the length equal to the width of two fingers plus some margin. In this way, if the person wrongly grasps the grip upside down, he would find this fact due to unusual feeling in grasping. Then the person re-grasps the grip correctly.

The lower grip section 72C further includes a projected portion 77 extending on a plane on which the palm of the person makes contact with the grip 72. The projected portion 77 acts to achieve good close contact of the palm with the measuring electrode 74.

More particularly, because of the lower grip section 72C only grasped with the medical and little fingers of the person, the grasping force applied thereby is lower than that for the upper grip section 72B. This does not achieve good close contact of the palm with the measuring electrode 74, and therefore, there may be any possibility that no reliable measurement can be attained. In order to solve such problem, the projected portion 77 is provided to assure the good close contact of the palm with the measuring electrode, irrespective of lower grasping force.

In the grip as shown in FIG. 6, the middle finger of the person is placed in the recess 72A, as described above. This means that other fingers of the person are limited in their contact positions on the grip. The diameter of the grip is fixed, and therefore, it is difficult to reliably hold the grip with the sufficient force by all the people from an adult whose hands are large to a child whose hands are small. Accordingly the grip in FIG. 6 can not always attain the desired stable contact condition for different persons under test.

Although not shown here, other handgrips known in the art are constructed in the same manner as above. Therefore, they can not easily be grasped by everybody and can attain no stable contact condition.

In view of the above, the present invention aims at providing a new and improved handgrip for use in bioelectrical impedance measurement, that allows the measurement always under a stable contact condition, irrespective of the size of a hand of the person under test. Further the present invention aims at providing a body fat measuring apparatus operated based upon the bioelectrical impedance measurement using the handgrip.

SUMMARY OF THE INVENTION

To attain those objects, the present invention provides a bioelectrical impedance measuring apparatus provided with a handgrip, a current source for supplying a measuring current into a body of a person under test via a current supplying electrode in contact with palm of the person, a voltage measuring unit for measuring a voltage on a voltage measuring electrode, and an arithmetic unit for calculating a bioelectrical impedance of the person based said current and said voltage, comprising the handgrip including a cylindrical grip section on which said current supplying electrode and said voltage measuring electrode are disposed each in parallel to an axis of said grip section, said cylindrical grip section gradually increasing in diameter from a portion thereof that is in contact with a thumb and a index fingers of the person toward a portion thereof that is in contact with a little finger of the person.

Preferably the handgrip further includes an auxiliary member coupled with said cylindrical grip section.

Preferably said current supplying electrode is disposed on a portion of the grip section that is contact with finger tips of the person in parallel to the axis of said grip section. In addition said voltage measuring electrode is disposed on a portion of the grip section that is contact with a palm and a thenar of the person in parallel to the axis of said grip section.

Preferably said current supplying electrode and said voltage measuring electrode are provided on each of a pair of handgrips for right and left hands of the person.

BRIEF DESCRIPTION OF THE DRAWINGS

The present invention will now be described in further detail with regard to preferred embodiments as illustrated in the accompanying drawings, in which.

DESCRIPTION OF THE PREFERRED EMBODIMENTS

A handgrip for use in bioelectrical impedance measurement according to the present invention is constructed in such manner that a grip section thereof to be grasped by a person under test is in the form of a cylinder, but it gradually increases in diameter from one end to another end. The grip section of the handgrip is provided with a current supplying electrode and a voltage measuring electrode that are disposed along the axial direction and spaced apart by the predetermined distance. The handgrip further includes an auxiliary member coupled with the grip section.

Now the present invention will be described in more detail with reference to the accompanying drawings.

Figure 1:
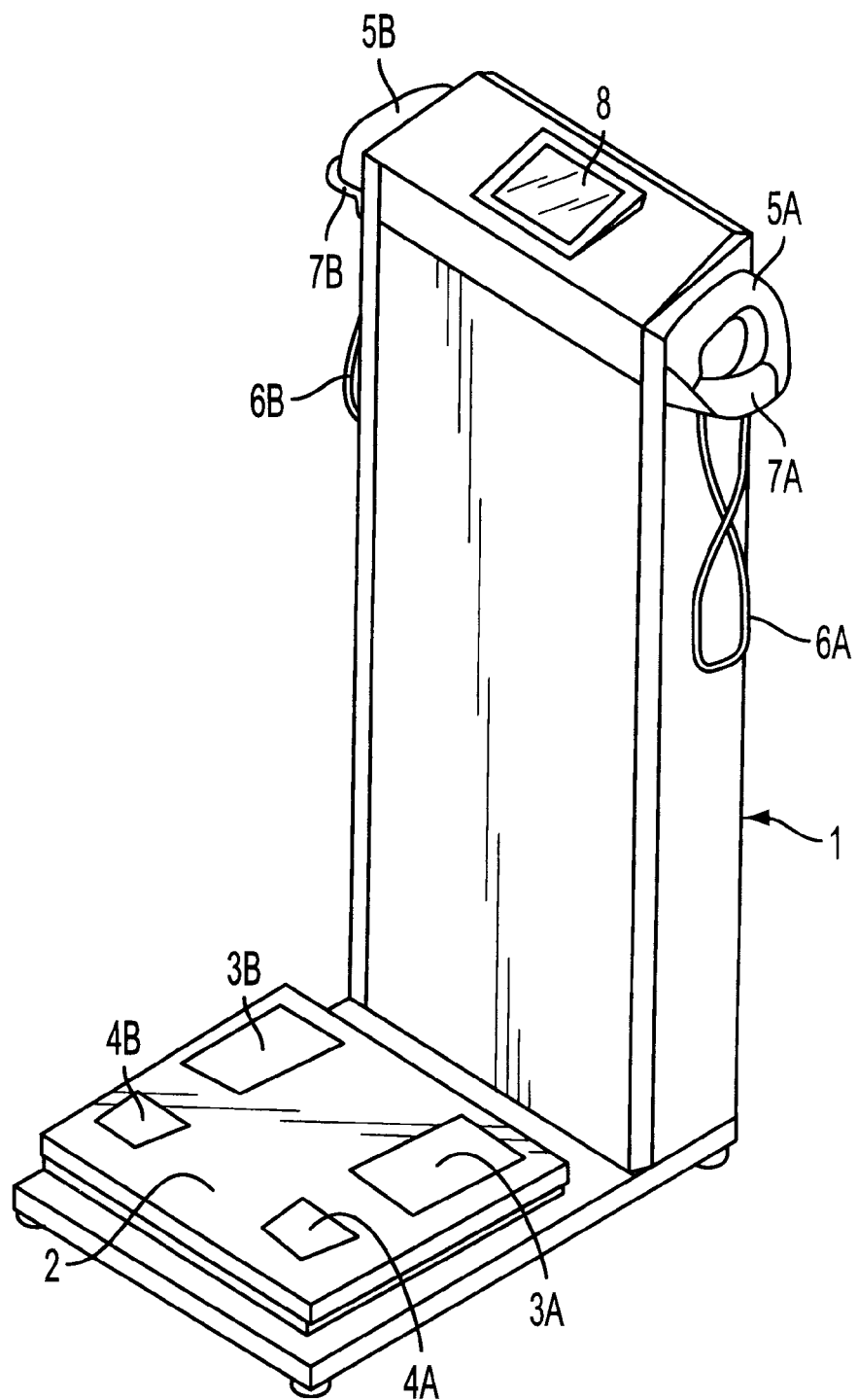
FIG. 1 is a perspective view representing a body fat measuring apparatus incorporating a handgrip according to the present invention.

FIG. 1 is a perspective view representing a body fat measuring apparatus 1 operated based on a biological impedance measurement. The body fat measuring apparatus 1 is provided with hand electrodes and foot electrodes for measuring an impedance for a whole body of the person. The body fat measuring apparatus 1 include an "L" shaped body comprising vertical and horizontal portions. A conventional weight meter 2 is mounted on the horizontal portion of the body fat measuring apparatus 1. The weight meter 2 includes foot electrodes 3A, 3B, 4A and 4B on the measuring plane thereof These foot electrodes are arranged to contact with soles of a person under test when performing the measurement. More specifically, the foot electrode 3A is contact with a toe of the right foot, and the foot electrode 3B is contact with a toe of the left foot of the person. Further the foot electrode 4A is contact with a heel of the right foot, and the foot electrode 4B is contact with a heel of the left foot of the person. The electrodes 3A and 3B act to supply an electric current to the body of the person under test. The electrodes 4A and 4B are used for voltage measurement.

The body fat measuring apparatus 1 further includes a right-hand-handgrip 5A and a left-hand-handgrip 5B held on the opposite sides of the vertical portion. The handgrips 5A and 5B are connected to the apparatus 1 via electric wires 6A and 6B, respectively. In addition, grip holders 7A and 7B are mounted on the apparatus 1 for holding the handgrips 5A and 5B, respectively. The grip holders are mainly used to hold the handgrips during the time period other than that for the bioelectrical impedance measurement.

Further, a display 8 is mounted on the top of the body fat measuring apparatus 1. The display 8 is formed by an LCD module with a touch panel (hereafter referred to as simply a "touch panel"). In addition to display the measurement result, personal information and waiting message, the display 8 has a data input function with the aid of the touch panel. Therefore, it is possible to enter the information such as height, sex, and age of the person under test and to enter other information by pushing some switches displayed on the touch panel.

Figure 2A:
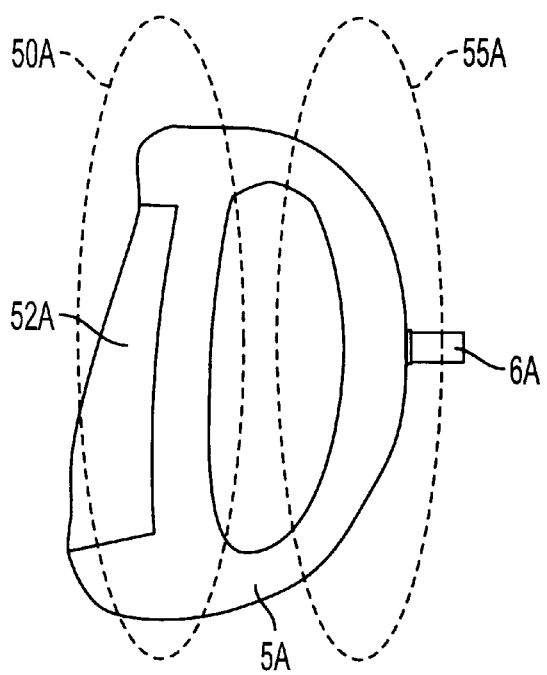
FIG. 2 is a side view representing the handgrip.
Figure 2B:
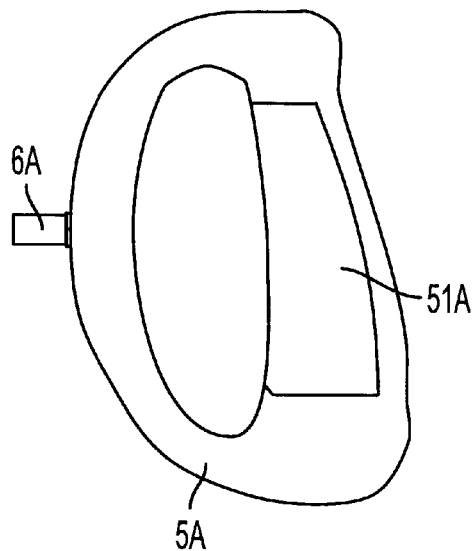
Figure 6:
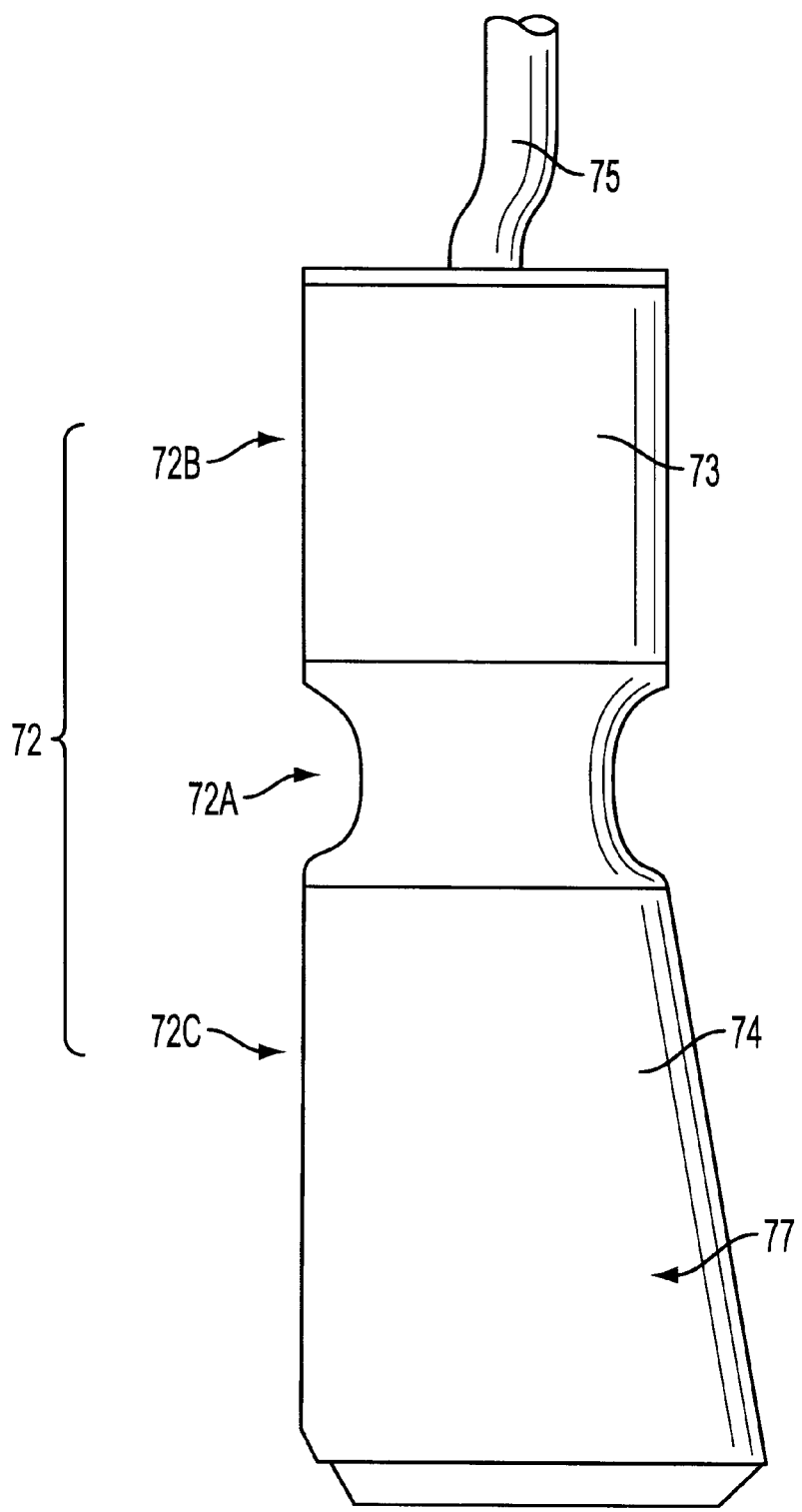
FIG. 6 is a view representing a prior art handgrip for use in bioelectrical impedance measurement.

Now, the handgrips 5A and 5B will be described in more detail. FIG. 2 is a side view representing the light-hand-handgrip 5A for the person. More specifically, FIG. 2(*a*) shows the handgrip 5A, as viewed from the outer side, and FIG. 2(*b*) also shows it, but as viewed from the inner side. As shown in FIG. 2, the handgrip has substantially arcuated shape and has a large oval hole in the center portion thereof. A curved auxiliary member 55A is added to the handgrip. The handgrip 5A includes a grip section 50A having a current supplying electrode 51A mounted at the inner side in the axial direction and a voltage measuring electrode 52A mounted at the outer side and at the symmetrical position to the current supplying electrode 51A. In addition, the grip section 50A is in the form of a cylinder having greater diameter at the bottom end than at the top end. The diameter of the grip section gradually increases from the top end to the bottom end. It is to be noted that the handgrip 5A of the present invention has no recess formed therein, as in the case of the prior art handgrip in FIG. 6.

Figure 3A:
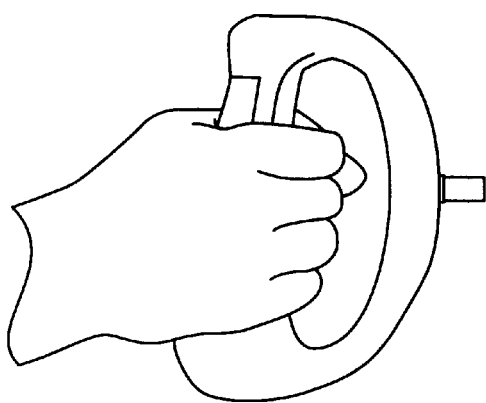
FIG. 3 is a view representing the condition wherein the handgrip is grasped by a hand.
Figure 3B:
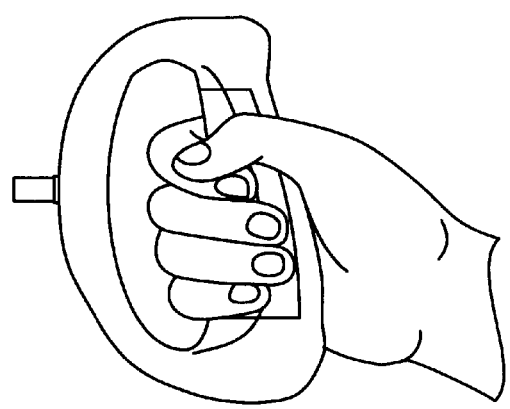

FIG. 3 shows the case where the handgrip according to the present invention is actually grasped by an adult person as the person under test. More particularly, FIG. 3(*a*) shows the right-hand-handgrip 5A grasped with the right hand of the person under test, as viewed from the outer side, and FIG. 3(*b*) also shows it, but as viewed from the inner side.

Referring to FIG. 3, when the adult person grasps the handgrip 5A, he grasps the grip section 50A of the handgrip at substantially middle position thereof. In general, when the person grasps the handgrip, the index and middle fingers of the person apply more strong force to the hand grip, and therefore, those fingers can be made close contact with the grip section 50A. According to the present invention, the grip section 50A gradually increases in the diameter towards the bottom end thereof. Therefore, the medical and little fingers having weaker grasping power can still surely make contact with the grip section 50A. Furthermore, because of the auxiliary member 55A coupled with the handgrip 50A, as shown in FIG. 2, the person under test can properly grasp the handgrip 5A without any positional error in forward-and-back direction of the handgrip. This can assure the stable contact condition between each finger and the current supplying electrode 51A, and between the thenar (i.e. the root of the thumb finger) and the voltage measuring electrode 52A.

Figure 4A:
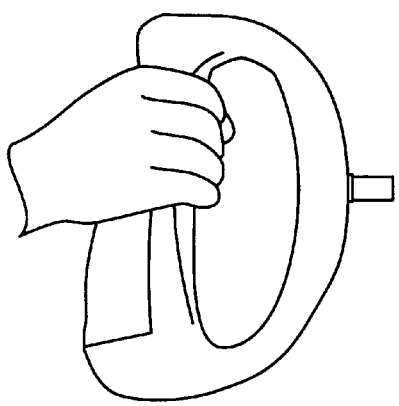
FIG. 4 is another view representing the condition wherein the handgrip is grasped by a hand.
Figure 4B:
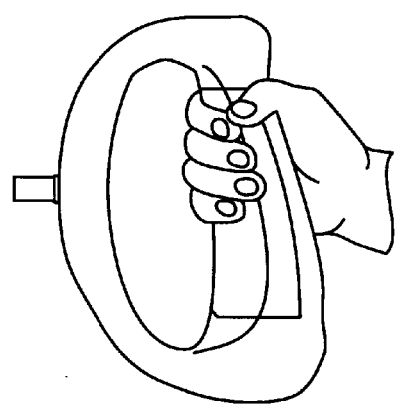

FIG. 4 shows the case where the handgrip according to the present invention is actually grasped by the person whose hand is small, such as a child. More particularly, FIG. 4(a) shows the right-hand-handgrip 5A grasped with the light hand of the person under test, as viewed from the outer side, and FIG. 4(b) also shows it, but as viewed from the inner side.

As shown in FIG. 4, when the person whose hand is small grasps the handgrip 5A, he grasps the grip section 50A of the handgrip at the upper portion thereof. In case of a child whose hand is, of course, small relative to an adult and has weaker grasping power than the adult, if the child would grasp the middle portion of the grip 50A of which diameter is greater, it becomes difficult to grasp it with sufficient force. As the result, the contact pressure to each of the electrodes 51A and 52A may fluctuate, which affects the contact impedance value as resulted from the impedance measurement. This, of course, leads to increase the error factor in measuring the bioelectrical impedance. According to the present invention, however, when the child grasps the handgrip, he, of course, grasps the upper portion of the grip 50A, as shown in FIG. 4, because it is the position to easily grasp by the child. Therefore, even the child can surely produce the stable contact between the finger ends and the current supplying electrode 51A, and between the thenar and the voltage measuring electrode 52A.

Although not shown here, for persons whose hands are more larger, such as American and European people, they grasp the entire grip section 50A. According to the present invention, however, due to the configuration of the grip section 50A whose diameter increases toward the bottom end thereof, even the medical and little fingers having lower grasping power can surely make contact with the grip section 50A. Therefore, the stable contact can again be produced between the finger ends and the current supplying electrode 51A, and between the thenar and the voltage measuring electrode 52A.

Then an operation of the body fat measuring apparatus incorporating the handgrip of the present invention will be described hereafter.

The circuit configuration of the body fat measuring apparatus 1 based upon the bioelectrical impedance measurement is not described here in detail, because it is already known in the art. It is suffice to say that the body fat measuring apparatus 1 includes a CPU for performing a various kind of arithmetic operation and control functions, and a constant current source for producing a constant current or a measuring current in response to the instruction from the CPU. The constant current source is connected at its output to the current supplying electrodes for feet 2A, 2B and the current supplying electrodes for hands 51A, 51B.

The voltage measuring electrodes 3A, 3B and 52A, 52B are connected to a voltage amplifier circuit in the body fat measuring apparatus 1. The apparatus 1 further includes a detection circuit for shaping the amplified voltage signal, and an A/D converter for converting the shaped, amplified voltage signal from analog form to digital form. The converted digital signal from the A/D converter is entered into the CPU. A weight sensor of the weight meter 2 is also connected to the CPU for calculating the weight value.

Also connected to the CPU is the display 8. This is formed by an LCD with a touch panel. The display 8 generally displays the body fat information such as the body fat percentage and the amount of body fat, as estimated based upon the bioelectrical impedance value and the weight value measured as well as the preset and stored personal information of the person under test. The display 8 also has the switching function on the touch panel. Accordingly the CPU calculates the bioelectrical impedance based on the measuring current fed into the body of the person and the voltage actually measured. Then the CPU estimates the body fat percentage and the amount of body fat from the calculated bioelectrical impedance value and the weight value, as well as the stored personal information, and thereafter, displays them on the display 8.

As regard to the sequence of the measuring operation, the person under test uses the touch panel on the display 8 as the data input means to enter the personal information such as height, sex and age in advance.

The measurement of the body fat for the person is actually started by pushing a measurement start switch on the touch panel by the person. The person gets on the weight meter 2 on the body fat measuring apparatus 1 with the bare soles of the person contact with the electrodes thereon. More particularly, the toe and the heel of the right foot are contact with the electrodes 3A and 4A,respectively. Similarly, the toe and the heel of the left foot are contact with the electrodes 3B and 4B,respectively. Then, the person under test should make contact the skin of his hands with the hand electrodes on the handgrip. Here, the description will be made only to the right-hand-handgrip 5A. The same can be applied to the left-hand-handgrip 5B.

The person under test picks up the handgrip 5A held in the grip holder 7A with his light hand. In other words, he grasps the grip section 50A of the handgrip 5A, as shown in FIG. 3. More specifically, each finger end is made contact with the current supplying electrode 51A and the thenar is made contact with the voltage measuring electrode 52A. Then the person drops both arms to take a pose for measurement, and thereafter, the measurement is started.

Figure 5:
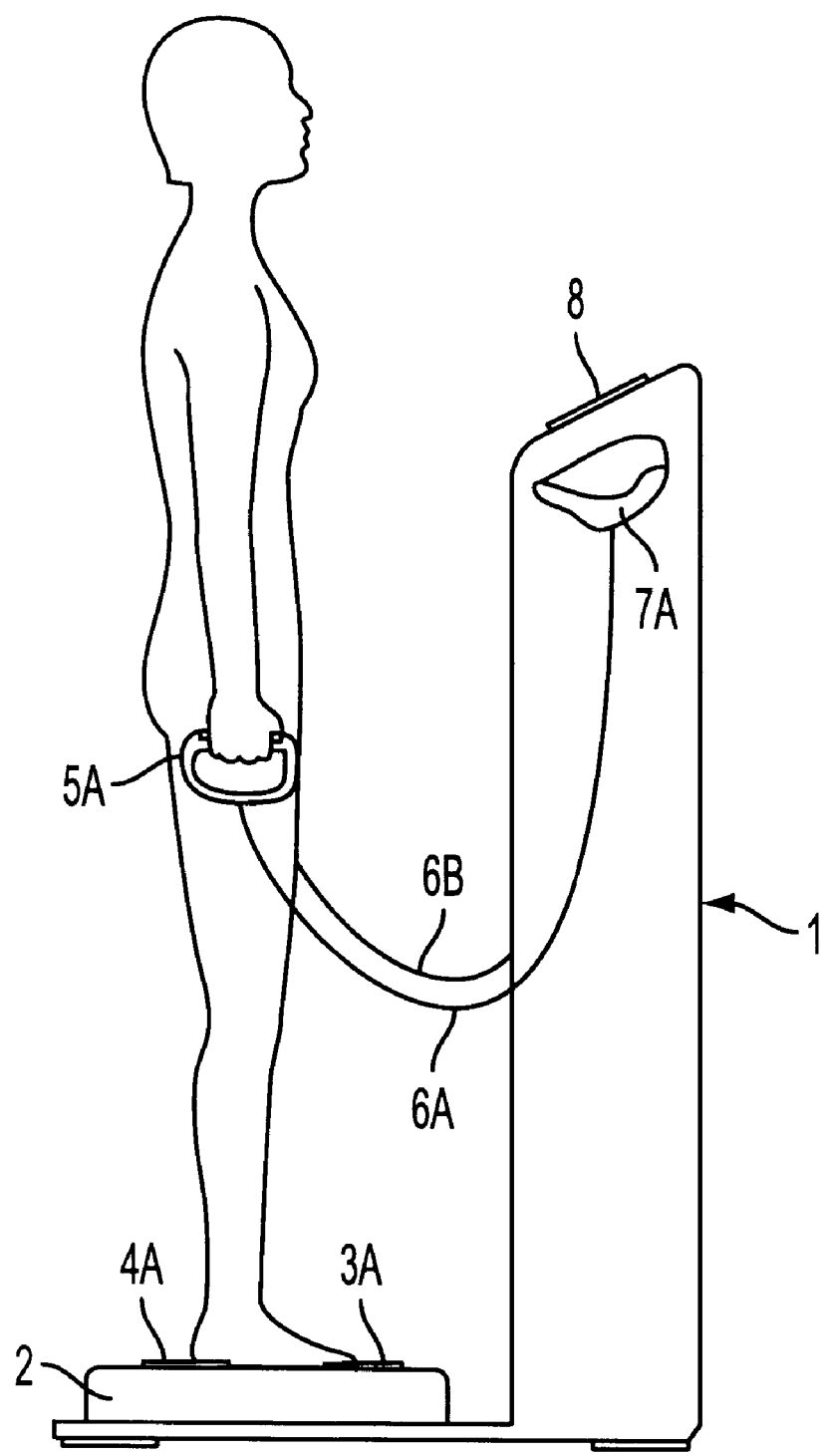
FIG. 5 is a view representing the condition wherein a person under test is conducting the measurement by the body fat measuring apparatus.

FIG. 5 is a side view representing the condition in which the person under test is actually conducting the measurement by the apparatus 1 having the handgrip of the present invention incorporated therein, as shown in FIG. 1. Referring to FIG. 5, the person under test stands on the weight meter with his soles making contact to the foot electrodes and with his both hands naturally depending while grasping the handgrips. With this condition, the measuring apparatus 1 first performs the measurement of weight of the person with the weight meter 2, and then, performs the measurement of bioelectrical impedance for the person. Thereafter, the apparatus 1 calculates the body fat percentage and the amount of body fat for whole body or any parts of the person, based upon the weight and the bioelectrical impedance thus measured, as well as the pre-stored personal information, and displays them on the display 8.

In the above description for the handgrip according to the present invention with reference to FIG. 2, the handgrip has been described, as being substantially arcuated shape and having a large oval hole in the center portion thereof. In addition, the handgrip has a curved auxiliary member 55A coupled thereto. The present invention, however, is not limited to such configuration of the handgrip, because the essential factor of the present invention is such that the grip section of the handgrip gradually increases in diameter.

Further, the body fat measuring apparatus has been described, as using the foot electrodes on the weight meter, in addition to the hand electrodes, for allowing the measurement of whole body and/or any parts of the person. However, the present invention is not limited to such construction of the measuring apparatus, because the present invention is directed toward the handgrip for use in the measuring apparatus based on the bioelectrical impedance measurement.

It is apparent from the foregoing that the present invention has provided a handgrip including a grip section whose diameter is small at the top end, but gradually increases toward the bottom end. The grip section has a current supplying electrode and a voltage measuring electrode mounted thereon in the axial direction. The grip section has no recess formed thereon for limiting the position at which a specified finger is placed, as in the case of the prior art handgrip. Therefore, all the people including those such as children whose hands are small and adults or American/European people whose hands are large can produce reliable and stable contact with the handgrip of the present invention. According to the present invention, the medical and little fingers of the person can still produce stable contact with the handgrip, irrespective of their lower grasping power, due to the construction thereof In addition, provision of the auxiliary member coupled with the grip section prevents the person from wrongly grasping the handgrip as to the forward-and-back direction. It becomes possible to surely hold the grip section with the finger in contact to the current supplying electrode and the thenar in contact to the voltage measurement electrode. This allows decrease in contact impedance that is a main factor of producing any erroneous measurement of the bioelectrical impedance. As the result, high precision measurement of the bioelectrical impedance can be attained.

Accordingly it is one of the advantages of the present invention that only one type of the handgrip can be adapted for use with several different people whose hands are at different size. For example, the present invention is significantly useful in an application, such as a group health examination, wherein a number of persons are to be measured at one time for the body fat. In such application, all the people can reliably be measured with the handgrip of the present invention.

Furthermore, when the handgrip of the present invention is used in an apparatus for measuring bioelectrical impedance of a person under test, it allows the reliable measurement for not only the impedance between both hands of the person, but also the impedance between either hand and either foot, as well as the impedance across any parts of the person, depending on what combination of hand electrodes and foot electrodes is used.

In case of the prior art grip as disclosed in TOKUKAIHEI No. 11-178806 and described above with reference to FIG. 6, the grip 72 is constructed in such manner that the person under test grasps the upper grip portion 72B on which the applying electrode 73 is disposed with his index finger and thumb finger, and the person grasps the lower grip portion 72C on which the measuring electrode 74 is disposed with his medical finger and little finger. Such construction of the grip 72 has deficiency in that it has small contact area for the voltage measurement portion, thereby affecting the result of measurement. In contrast thereto, according to the present invention, the finger tips of the person can surely be made contact with the current supplying electrode and the thenar of the person can surely be made contact with the voltage measuring electrode. This assures that sufficiently large contact area is maintained for the measurement. Therefore the present invention can eliminate any error factor resulting from less contact area for the voltage measurement portion of the prior grip, which allows higher precision of the impedance measurement.

What is claimed is:

1. A bioelectrical impedance measuring apparatus provided with, a handgrip, a current source for supplying a measuring current into a body of a person under test via a current supplying electrode in contact with a palm of the person;

a voltage measuring unit for measuring a voltage on a voltage measuring electrode; and an arithmetic unit for calculating a bioelectrical impedance of the person based on said current and said voltage, comprising:

the handgrip including a cylindrical grip section on which said current supplying electrode and said voltage measuring electrode are disposed each in parallel to an axis of said grip section, in positions symmetrical to each other with respect to said axis of said grip section, and extending only partially around said axis of said grip section; and said cylindrical grip section gradually increasing in diameter from a portion thereof that is in contact with a thumb and a index fingers of the person toward a portion thereof that is in contact with a little finger of the person.

2. A bioelectrical impedance measuring apparatus according to claim 1 in which said handgrip further comprises an auxiliary member coupled with said cylindrical grip section.

3. A bioelectrical impedance measuring apparatus according to claim 1 in which said current supplying electrode is disposed on a portion of the grip section for contacting only the finger tips of the person in parallel to the axis of said grip section, and said voltage measuring electrode is disposed on a portion of the grip section for contacting only a palm and a thenar of the person in parallel to the axis of said grip section.

4. A bioelectrical impedance measuring apparatus according to claim 1 in which it comprises a pair of handgrips for right and left hands of the person, each of the handgrips being separate from each other and from a main body of the apparatus, said current supplying electrode and said voltage measuring electrode being provided on each handgrips.

* * * * *